(12) United States Patent
Maznev et al.

(10) Patent No.: US 10,241,058 B2
(45) Date of Patent: Mar. 26, 2019

(54) SYSTEMS AND METHODS FOR QUALITY CONTROL OF A PERIODIC STRUCTURE

(71) Applicants: Alexei Maznev, Allston, MA (US); Keith A. Nelson, Newton, MA (US); Abdelhak Bensaoula, Houston, TX (US); Jateen S. Gandhi, Houston, TX (US); Donna Washington Stokes, Friendswood, TX (US); Rebecca Lynne Forrest, Houston, TX (US); Hyun Doug Shin, Cambridge, MA (US)

(72) Inventors: Alexei Maznev, Allston, MA (US); Keith A. Nelson, Newton, MA (US); Abdelhak Bensaoula, Houston, TX (US); Jateen S. Gandhi, Houston, TX (US); Donna Washington Stokes, Friendswood, TX (US); Rebecca Lynne Forrest, Houston, TX (US); Hyun Doug Shin, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/641,724

(22) Filed: Jul. 5, 2017

(65) Prior Publication Data
US 2018/0011031 A1 Jan. 11, 2018

Related U.S. Application Data

(60) Provisional application No. 62/358,219, filed on Jul. 5, 2016.

(51) Int. Cl.
*G01N 21/95* (2006.01)
*G01K 11/00* (2006.01)
(Continued)

(52) U.S. Cl.
CPC ..... *G01N 21/9515* (2013.01); *G01N 21/1717* (2013.01); *G01N 21/8422* (2013.01);
(Continued)

(58) Field of Classification Search
CPC .......... G01N 21/9515; G01N 21/1717; G01N 21/8422; G01N 21/9501; G01N 29/38;
(Continued)

(56) References Cited

U.S. PATENT DOCUMENTS 4,710,030 A 12/1987 Tauc et al.
5,748,318 A * 5/1998 Maris ................. G01N 21/1702
356/630

(Continued)

OTHER PUBLICATIONS

A. C. Diebold and R. Stoner, in Handbook of Silicon Semiconductor Metrology, edited by A. C. Diebold (Dekker, New York, 2001), pp. 197-214.
(Continued)

*Primary Examiner* — Sang H Nguyen
(74) *Attorney, Agent, or Firm* — Smith Baluch LLP

(57) ABSTRACT

Quality control of a periodic structure is performed using the damping rate of acoustic waves generated in the periodic structure. In this technique, an excitation light beam illuminates the first layer in the periodic structure to excite an acoustic wave. Possible irregularities in the periodic structure can scatter the acoustic wave, thereby increasing the damping rate of the acoustic wave. A sequence of probe light beams illuminates the periodic structure to measure the acoustic wave as a function of time to generated a temporal signal representing the damping rate of the acoustic signal. The acquired damping rate is employed to evaluate the quality of the periodic structure.

16 Claims, 7 Drawing Sheets

(51) Int. Cl.
*G10K 11/00* (2006.01)
*G01N 21/17* (2006.01)
*G01N 21/84* (2006.01)
*G01N 29/24* (2006.01)
*G01N 29/38* (2006.01)
*G01N 29/46* (2006.01)

(52) U.S. Cl.
CPC ..... *G01N 21/9501* (2013.01); *G01N 29/2418* (2013.01); *G01N 29/38* (2013.01); *G01N 29/46* (2013.01); *G10K 11/002* (2013.01); *G01N 2021/8438* (2013.01); *G01N 2291/0231* (2013.01); *G01N 2291/0237* (2013.01); *G01N 2291/02854* (2013.01); *G01N 2291/2697* (2013.01)

(58) Field of Classification Search
CPC ............... G01N 29/46; G01N 29/2418; G01N 2291/2697; G01N 2291/0237; G01N 2291/0231; G01N 2291/02854; G01N 2021/8438; G01K 11/002
See application file for complete search history.

(56) References Cited

U.S. PATENT DOCUMENTS

| | | | |
|---|---|---|---|
| 5,956,735 A | 9/1999 | Clark et al. | |
| 6,038,026 A | 3/2000 | Maris | |
| 6,175,416 B1* | 1/2001 | Maris | G01N 21/1702 356/432 |
| 6,256,100 B1* | 7/2001 | Banet | G01B 11/0666 356/432 |
| 6,321,601 B1 | 11/2001 | Maris | |
| 6,348,967 B1* | 2/2002 | Nelson | G01B 11/0666 356/432 |
| 6,393,915 B1 | 5/2002 | Banet et al. | |
| 6,400,449 B2 | 6/2002 | Maris et al. | |
| 6,532,070 B1* | 3/2003 | Hovinen | G01N 21/171 356/369 |
| 7,365,864 B2 | 4/2008 | Gostein et al. | |
| 8,567,253 B2* | 10/2013 | Maris | A61B 5/0097 73/642 |
| 2003/0112451 A1* | 6/2003 | Mautz | B24B 37/04 356/630 |
| 2004/0174529 A1* | 9/2004 | Maznev | G01B 11/0666 356/502 |
| 2004/0196453 A1* | 10/2004 | Some | G01N 25/72 356/237.1 |
| 2006/0012782 A1 | 1/2006 | Lim et al. | |
| 2006/0094133 A1* | 5/2006 | Takeuchi | G01N 21/1717 438/14 |
| 2009/0212769 A1* | 8/2009 | Stoica | G01R 33/032 324/244.1 |
| 2012/0236307 A1* | 9/2012 | Sekiguchi | B82Y 20/00 356/402 |

OTHER PUBLICATIONS

Chi-Kuang Sun, Jian-Chin Lang, and Xiang-Yang Yu, "Coherent Acoustic Phonon Oscillations in Semiconductor Multiple Quantum Wells with Piezoelectric Fields,"*Phys. Rev. Lett.*, vol. 84, No. 1, pp. 179-182 (Jan. 2000).

G. Andrew Antonelli, Humphrey J. Maris, Sandra G. Malhotra, and James M. E. Harper, "Picosecond ultrasonics study of the vibrational modes of a nanostructure," *J. Appl. Phys.*, vol. 91, No. 5, pp. 3261-3267 (Mar. 2002).

International Search Report and Written Opinion dated Sep. 15, 2017 from International Application No. PCT/US2017/040686, 14 pages.

M. Gostein, P. Lefevre, A.A. Maznev, and M. Joffe, MRS Symposium Proceedings, vol. 671 (Materials Research Society, Warrendale, 2001), pp. M3.9.1-M3.9.6.

Tzu-Ming Liu, Shih-Ze Sun, Chieh-Feng Chang, Guan-Ting Chen, Chang-Chi Pan, Jen-Inn Chyi, and Chi-Kuang Sun, "Roles of Dislocation Density to the Scattering of Nano-acoustic Waves in GaN," *Chinese Journal of Physics*, vol. 49, No. 1, pp. 171-175 (Feb. 2011).

\* cited by examiner

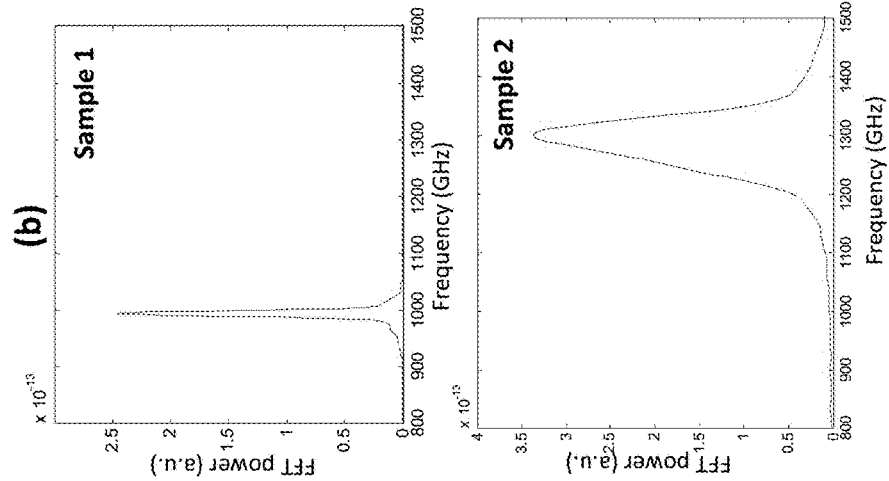
FIG. 6B
FIG. 6D
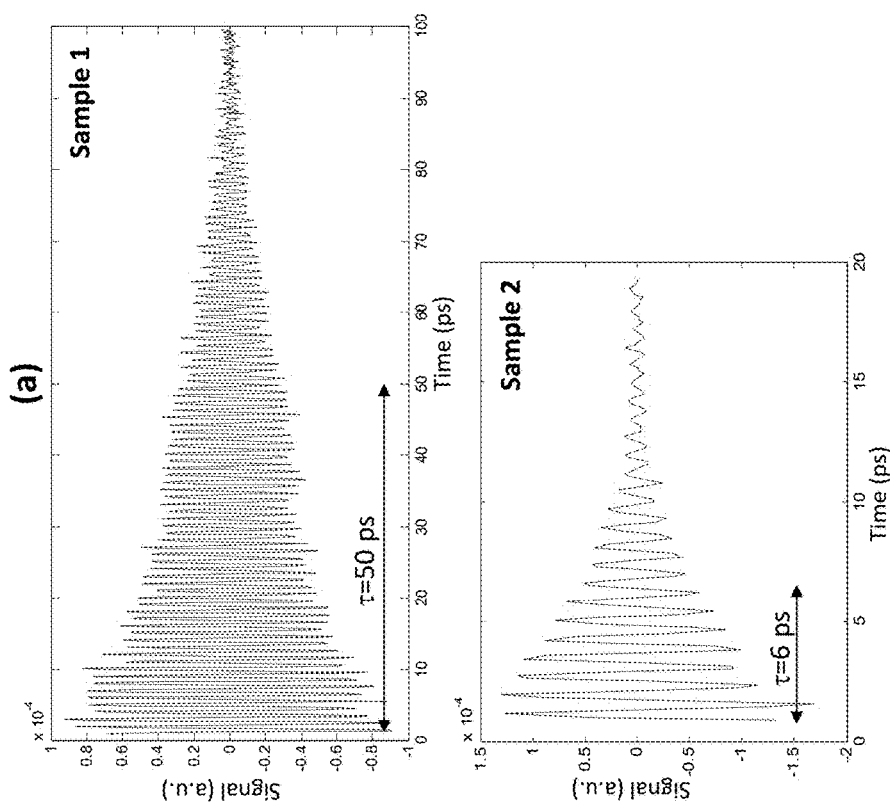
FIG. 6A
FIG. 6C

SYSTEMS AND METHODS FOR QUALITY CONTROL OF A PERIODIC STRUCTURE

CROSS-REFERENCES TO RELATED APPLICATIONS

This application claims the priority benefit under 35 U.S.C. § 119(e) of U.S. Application No. 62/358,219, filed Jul. 5, 2016, entitled "METHOD OF ASSESSING UNIFORMITY OF PERIODIC STRUCTURES BASED ON THE DECAY TIME OF LASER-GENERATED ACOUSTIC VIBRATIONS," which is hereby incorporated herein by reference in its entirety.

GOVERNMENT SUPPORT

This invention was made with Government support under Grant No. DE-SC0001299 awarded by the Department of Energy. The Government has certain rights in the invention.

BACKGROUND

Modern semiconductor devices usually include multilayer structures or other periodic structures. For example, thin films of dielectric materials (e.g., polymer, oxide) and conducting materials (e.g., metal) are used in a range of microelectronic, optical, and biomedical devices. For example, GaN-based light emitting diodes (LEDs) often contain periodic superlattice structures made of alternating GaN and InGaN layers. Irregularities in these multilayer structures, such as deviations from expected periodicity and irregular interfaces between adjacent layers, can modify the electrical and mechanical properties of the structures, thereby affecting the performance of the resulting devices. Accordingly, it is desirable to monitor and control the dimensions of these multilayer structures more precisely.

One conventional approach to measuring the dimension of a multilayer structure is via imaging techniques. For example, in scanning electron microscopy (SEM), an electron beam is focused onto a small spot on a sample structure. Electrons that are scattered from the sample surface are detected to produce an image of the sample. This technique can have high contrast but is usually time consuming. In addition, the measurement is typically conduced in a high vacuum chamber, thereby increasing the cost and complexity of the measurement.

In another approach, a femtosecond laser is employed to generate acoustic waves in a periodic multilayer stack. In this case, the acoustic signal generated in the structure is periodic in time, with the period T depending on the spatial period d of the multilayer stack. Therefore, the average period of the multilayer stack can be derived from the frequency $f=1/T$ of acoustic oscillations. However, the frequency of the acoustic oscillations may not reveal any irregularities or non-uniformities in the multilayer structure, thereby limiting its use in quality assurance of multilayer structures.

SUMMARY

Embodiments of the present invention include apparatus, systems, and methods for quality control of a periodic structure. In one example, a method of quality control of a periodic structure including a stack of layers is disclosed. The method includes illuminating the periodic structure through a first layer in the stack of layers with at least one excitation light beam. The excitation light beam excites an acoustic wave in the periodic structure. The method also includes illuminating the periodic structure with at least one probe light beam and detecting the at least one probe light beam, using a photodetector, after interaction with the periodic structure, as to generate a signal representing a damping rate of the acoustic wave. The method also includes estimating a quality of the periodic structure based at least in part on the damping rate of the acoustic wave in the periodic structure.

In another example, an apparatus for evaluating quality of a periodic structure comprising a stack of layers is disclosed. The apparatus includes at least one light source configured to illuminate the periodic structure through a first layer in the stack of layers with an excitation light beam. The excitation light beam excites an acoustic wave in the periodic structure. The at least one light source is further configured to illuminate the periodic structure with a probe light beam. The apparatus also includes a detection system, in optical communication with the periodic structure, to detect the probe light beam after interaction with the periodic structure so as to generate a signal representing a damping rate of the acoustic wave in the periodic structure. The damping rate of the acoustic wave represents the quality of the periodic structure.

In yet another example, a method of estimating quality of a periodic structure comprising a stack of layers is disclosed. The method includes focusing a sequence of excitation light beams onto a first layer in the stack of layers. Each excitation light beam in the sequence of light beams has a pulse duration substantially equal to or less than 1 ps and a focal spot substantially equal to or less than 100 µm. Each excitation light beam excites an acoustic wave in the periodic structure. The method also includes focusing a sequence of probe light pulses onto the first layer in the stack of layers. Each probe light pulse in the sequence of probe light pulses has a distinct time delay with respect to a corresponding excitation light beam in the sequence of excitation light beams. The method also includes detecting each probe light pulse after transmission through at least a portion of the periodic structure so as to generate a signal representing a damping rate of the acoustic wave in the periodic structure and estimating the uniformity of the periodic structure based on the damping rate of the acoustic wave.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 6A and 6C show the measured acoustic signals generated in the superlattice structures shown in FIG. 5A.

FIGS. 6B and 6D show the spectral signals acquired by Fourier transform of the signal shown in FIG. 6A and 6C, respectively.

DETAILED DESCRIPTION

Systems, methods, and apparatus described herein employ the damping rate of an acoustic wave excited in a periodic structure (e.g., a multilayer structure) to more accurately monitor the quality of the periodic structure. In this approach, an excitation light beam is delivered to the first layer in the periodic structure (e.g., the top layer, the bottom layer, or the side layer) to excite an acoustic wave in the periodic structure. Small-scale non-uniformities in the periodic structure, such as irregularities at or on the interface between adjacent layers or other deviation from the desired dimensions, can scatter the acoustic wave, thereby decreasing the damping rate (also referred to as the decay time) of the acoustic wave. Accordingly, detecting the damping rate of the acoustic wave can provide insight into the quality of the periodic structure.

Exciting the acoustic wave via the first layer in the periodic structure can have several advantages over conventional methods, where the excitation light beam usually illuminates the entire periodic structure. First, many periodic structures in semiconductor devices may be buried in or blocked by one or more other components (e.g., oxide layers) such that it is not convenient or practical to illuminate the entire structure. Second, exciting the acoustic wave via the first layer allows the excitation light beam to be focused into a small spot (e.g., less than 100 µm in diameter). In other words, the acoustic wave can be excited by a local spot on the first layer absorbing the excitation light beam. As a result, the pulse energy used for acoustic wave excitation can be reduced.

Systems for Quality Control of Periodic Structures

Figure 1A:
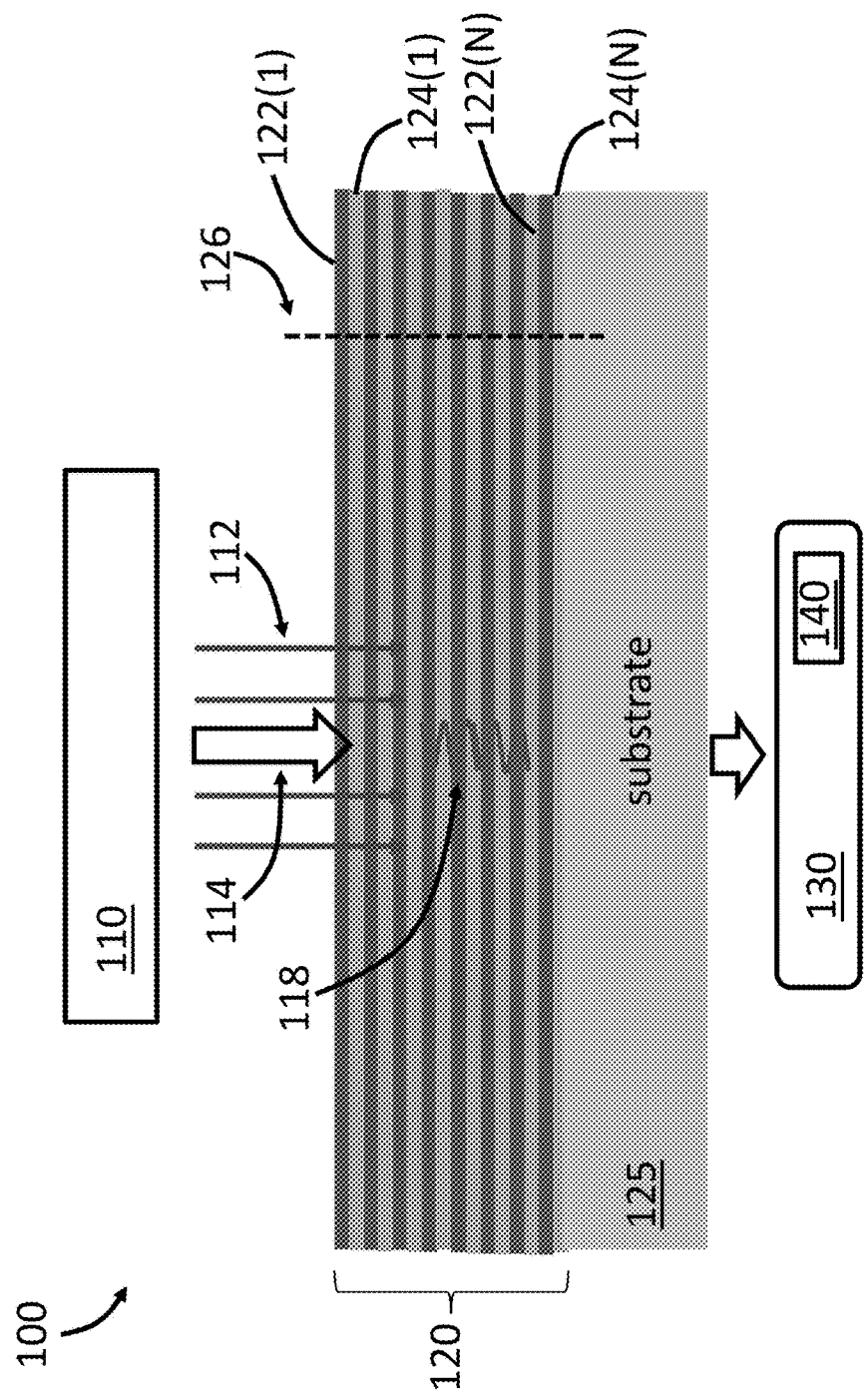
FIGS. 1A and 1B illustrate a system for quality control of a periodic structure based on the damping rate of acoustic waves excited in the periodic structure.

FIG. 1A shows a schematic of a system 100 for quality control of a periodic structure 120 based on the damping rate of acoustic waves excited in the periodic structure. The system 100 includes a light source 110 to emit excitation light beams 112 (also referred to as excitation light pulses 112) and probe light beams 114 (also referred to as probe light pulses 114) toward the periodic structure 120. The periodic structure 120 includes a stack of alternating layers 122 (including 122(1) to 122(N)) and 124 (including 124(1) to 124(N)). The first layers 122 can include a first material and the second layers 124 can include a second material having a different property (e.g., a different refractive index or absorption) than the first material. An optional substrate 125 can be used to support the periodic structure 120.

The excitation light beams 112 are directed to the first layer 122(1) to excite an acoustic wave 118 in the periodic structure 120. The first layer 122(1) absorbs at least a portion of the excitation light beams 112. The absorption increases the temperature of the first layer 122(1) and causes the layer to expand, thereby creating a strain pulse that propagates through the periodic structure, i.e., an acoustic wave. The acoustic wave 118 can change the density distribution of the periodic structure 120, thereby modulating the probe light beams 114 propagating in the periodic structure 120. For example, the change of density distribution within the periodic structure 120 can change the dielectric function (including both real part and imaginary part) of the periodic structure 120 and accordingly change the reflectivity and/or the transmission of the periodic structure 120 to the probe light beams 114. More details of acoustic wave excitation and probe beam modulation can be found in U.S. Pat. No. 6,321,601, entitled "Optical method for the characterization of laterally-patterned samples in integrated circuits," which is hereby incorporated herein by reference in its entirety.

The probe light beams 114 transmitted through the periodic structure 120 are detected by a detection system 130, which can include, for example, a photodetector. The detected signals can then be used to derive information about the acoustic wave 118, including the frequency and damping rate of the acoustic wave.

The system 100 can detect a variety of irregularities (also referred to as non-uniformity) that can affect the quality of the periodic structure 120. In one example, the irregularity can include the deviation of the period from an expected period. For example, the periodic structure 120 may be expected to have a uniform period across the thickness, i.e., each pair of layers 122 and 124 may have the same thickness. However, the actual thickness of one or more pairs may be different from the expected period. This deviation can be manifested in the detected acoustic signal (see more details below). In another example, the irregularities can include a deviation from an expected flatness of the interface between adjacent layers. This type of irregularity is also referred to as interface roughness. In yet another example, the irregularities can include defects in the periodic structure 120, such as dislocations, voids, or any other defects that can affect the propagation of the probe light beams 114.

In one example, the excitation light beams 112 and/or the probe light beams 114 may be collimated. In another example, the excitation light beams 112 and/or the probe light beams 114 are focused onto the periodic structure 120. The diameter of the focal spot of the excitation light beams 112 and/or the probe light beams 114 can be, for example, about 5 µm to about 200 µm (e.g., about 5 µm, about 10 µm, about 20 µm, about 30 µm, about 50 µm, about 100 µm, about 150 µm, or about 200 µm, including any values and sub ranges in between).

In one example, the focal spot size of the excitation light beams 112 can be larger than the focal spot size of the probe light beams 114 (e.g., about 10% larger, about 20%, about 30% larger, about 50% larger, about 100% larger, about twice larger, about three time larger, about five times larger, or about ten times larger, measured in diameter). In another example, the focal spot size of the excitation light beams 112 can be substantially equal to the focal spot size of the probe light beams 114.

The pulse duration of the excitation light beams 112 can be substantially equal to or less than 1 ns (e.g., about 1 ns, about 500 ps, about 200 ps, about 100 ps, about 50 ps, about 20 ps, about 10 ps, about 5 ps, about 1 ps, about 500 fs, about 300 fs, about 200 fs, about 100 fs, or less, including any values and sub ranges in between). In one example, the pulse duration of the probe light beams 114 can be substantially equal to the pulse duration of the excitation light beams 112 (e.g., see FIG. 2 and descriptions below). In another example, the pulse duration of the probe light beams 114 can be smaller than the pulse duration of the excitation light beams 112.

The pulse energy of the excitation light beams 112 can depend on, for example, the focal spot size and the absorption coefficient of the first layer 122(1). In one example, the pulse energy of the excitation light beams 112 can be about 10 nJ to about 1 mJ (e.g., about 10 nJ, about 20 nJ, about 30 nJ, about 50 nJ, about 100 nJ, about 200 nJ, about 300 nJ, about 500 nJ, or about 1 mJ, including any values and sub ranges in between). The pulse energy of the probe light beams 114 can be about 0.5 nJ to about 20 nJ (e.g., about 0.5 nJ, about 1 nJ, about 2 nJ, about 3 nJ, about 4 nJ, about 6 nJ, about 8 nJ, about 10 nJ, about 12 nJ, about 15 nJ, or about 20 nJ, including any values and sub ranges in between).

In FIG. 1A, the excitation light beams 112 are substantially perpendicular to the surface of the first layer 122(1). In other words, the direction of the excitation light beams 112 is substantially parallel to the normal axis 126 of periodic structure 120 (or the direction of periodicity of the periodic structure 120). In practice, the excitation light beams 112 can propagate at an oblique angle with respect to the normal axis 126 (e.g., about 5°, about 10°, about 15°, about 20°, about 25°, about 30°, about 35°, about 40°, or about 45°, including any value and sub ranges in between). Similarly, the probe light beams 114 can also have an oblique angle with respect to the normal axis 126.

In some cases, the excitation light beams 112 and the probe light beams 114 can be directed to the periodic structure from different directions. For example, the excitation light beams 112 can be directed to the top layer 122(1), while the probe light beams 114 can be directed to the bottom layer 124(N). In another example, the excitation light beams 112 can be directed substantially parallel to the normal axis 126, while the probe light beams 114 can propagate at an oblique angle with respect to the normal axis 126.

In some cases, the excitation light beams 112 can include a sequence of excitation light pulses and the probe light beams 114 can also include a sequence of probe light pulses. Each excitation light pulse has a corresponding probe light pulse, but with a distinct time delay. For example, the ith excitation light pulse and the ith probe light pulse forms a pair and has a time delay $\Delta t_i$, where i=1, 2, . . . , N, is a positive integer and N is the total number of pulses in the sequence of excitation/probe light pulses. In this configuration, the ith excitation light pulse excites the acoustic wave and the ith probe light pulse measures the excited acoustic wave so as to acquire a signal representing the temporal evolution of the acoustic signal. The step size of the time delay (i.e. different between adjacent $\Delta t_i$, or $\Delta t_i - \Delta t_{i-1}$) can be, for example, about 50 fs to about 200 fs (e.g., about 50 fs, about 100 fs, about 150 fs, or about 200 fs, including any values and sub ranges in between). The maximum time delay $\Delta t$ can be, for example, about 20 ps to about 1 ns (e.g., about 20 ps, about 50 ps, about 100 ps, about 200 ps, about 500 ps, or about 1 ns, including any values and sub ranges in between).

In one example, each pair of excitation and probe light pulses can have a distinct time delay $\Delta t_i$. In another example, a group of excitation/probe pulse pairs can have the same time delay $\Delta t$ and the signal detected with these pairs can be averaged to increase the signal-to-noise ratio. Different groups of excitation/probe pulse pairs can have different time delays $\Delta t$ to capture the temporal evolution of the acoustic wave. The number of excitation/probe light pairs in each group can be, for example, about 5 to about 100 (e.g., about 5, about 10, about 20, about 30, about 50, or about 100, including any values and sub ranges in between).

In one example, the excitation light beams 112 and the probe light beams 114 are provided by a single laser. A splitter can be used to split a portion of the laser output as the excitation light beams 112 and another portion as the probe light beams 114 (see FIG. 2, described below). In another example, two different lasers can be used to deliver the excitation light beams 112 and the probe light beams 114. These lasers can be synchronized to control the delay between the excitation light beams 112 and the probe light beams 114.

The periodic structure 120 can include a multilayer structure on microscale or nanoscale. For example, the thickness of each layer (i.e., 122 or 124) can be about 1 nm to about 50 μm (e.g., about 1 nm, about 2 nm, about 3 nm, about 5 nm, about 10 nm, about 20 nm, about 50 nm, about 100 nm, about 200 nm, about 500 nm, about 1 μm, about 2 μm, about 3 μm, about 5 μm, about 10 μm, about 20 μm, or about 50 μm, including any values and sub ranges in between). The period variation that can be detected by the system 100 can be a fraction of the layer thickness. For example, the detectable variation (also referred to as system resolution, system sensitivity, or system precision) can be substantially equal to greater than 1% of the layer thickness (e.g., about 1%, about 2%, about 5%, about 10%, or about 20%, including any values and sub ranges in between). In practice, the system can be on the sub-nanometer scale (e.g., 1 nm or less).

The material of the periodic structure 120 can include metal, semiconductor, or a dielectric material. For example, the periodic structure 120 can include a semiconductor superlattice. As used herein, a semiconductor superlattice refers to a periodic structure including alternating layers of different materials and each layer is on the nano-scale. In another example, the periodic structure 120 can include alternating layers of metal and semiconductor, alternating layers of metal and dielectric, or alternating layers of semiconductor and dielectric.

In one example, the periodic structure 120 can be substantially transparent to the excitation light beams 112 and the probe light beams 114. In other words, the excitation light beams 112 and the probe light beams 114 can propagate through all the layers 122 and 124 in the periodic structure. In this case, the first layer 122(1) may absorb only a small amount of the excitation light beams 112 to excite the acoustic wave 118. The transparency of the periodic structure 120 can be described in term of the 1/e attenuation length of the excitation light beams 112, i.e., the distance at which the intensity of the excitation light beams 112 decreases to 1/e (about 36.8%) of the incident intensity. For example, the attenuation length of the excitation light beams 112 can be substantially equal to or greater than the thickness of the periodic structure 120 (e.g., one time greater, two times greater, three time greater, five times greater, ten times greater, or even more). The attenuation length of the probe light beams 114 can be similar to that of the excitation light beams 112.

In another example, the periodic structure 120 can be substantially transparent to the excitation light beams 112 but opaque to the probe light beams 114. In this case, the detection system 130 can be disposed to collect the probe light beams 114 reflected from the periodic structure 120. The attenuation length of the probe light beams 114 can be less than the thickness of the periodic structure 120.

Figure 1B:
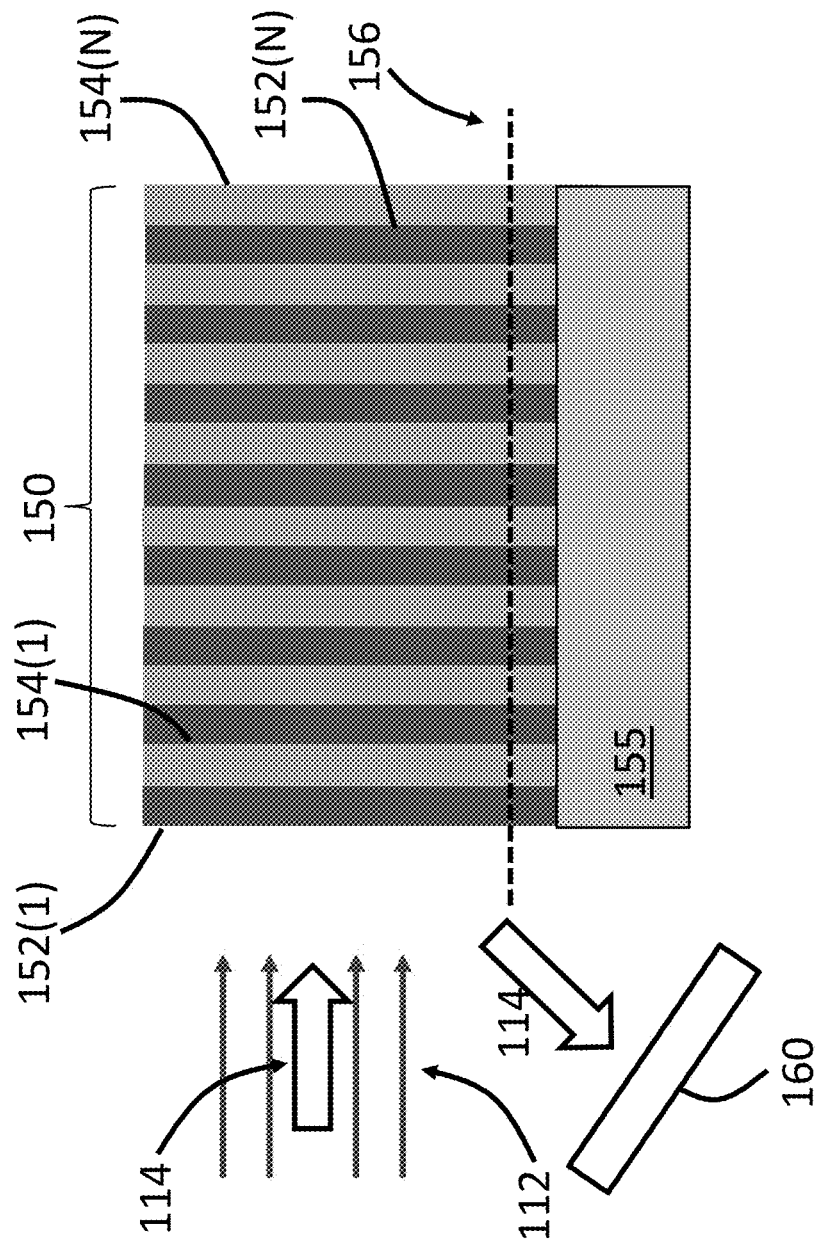

In FIG. 1A, the stack of layers 122 and 124 are parallel to the underlying substrate 125. Alternatively, the layers can be perpendicular to the supporting substrate as in FIG. 1B, which shows a schematic of a periodic structure 150 disposed on a substrate 155. The layers 152 (including 152(1) to 152(N)) and 154 (including 154(1) to 154(N)) in the periodic structure 150 define a normal axis 156 that is substantially parallel to the plane of the substrate 155. In this case, the excitation light beams 112 and the probe light beams 114 are delivered from the side direction and onto the first layer 152(1) in the stack. FIG. 1B also shows a detector 160 to detect the probe light beams 114 reflected from the periodic structure 150 and similar detection configurations can also be used in the system shown in FIG. 1A.

The detection system 130 can include a photodetector to detect the probe light beams 114 after interaction with the periodic structure 120 (e.g., transmission or reflection) as a function of time delay between the probe light beams 112 and the excitation light beams 112. The detected signals at different time delays can be compiled together to form a temporal signal that represents the temporal evolution of the acoustic signal (see, e.g., FIGS. 6A and 6C below).

Several methods can be used to estimate the quality of the periodic structure 120 based on the temporal signal. In one example, the acquired temporal signal can be curve fitted to an ideal sinusoidal waveform (or cosine waveform) to acquire the damping rate. In another example, Fourier transform can be carried out on the temporal signal to acquire a spectral signal including a spectral peak at the frequency of the acoustic wave. The damping rate of the acoustic signal can then be derived from the spectral width of the spectral peak at the frequency of the acoustic signal. In yet another example, an evaluator can observe the temporal signal and estimate the damping rate (and accordingly the quality of the periodic structure) subjectively.

In one example, the acquired damping rate of the acoustic signal can be compared with a threshold damping rate (or a desired damping rate). If the acquired damping rate is greater than a desired damping rate, a warning signal can be generated to indicate that the periodic structure 120 is defective. Alternatively or additionally, the periodic structure can be rejected for further processing (e.g., packaging or sale). This method can be used for a fast quality check of manufactured products including periodic structures.

In another example, the acquired damping rate of the periodic structure (here referred to as a sample periodic structure) can be compared with expected damping rates in a lookup table. Each of the expected damping rates can be acquired from a reference periodic structure. The dimensions of the reference periodic structures can be acquired via, for example, imaging techniques such as transmission electron microscopy (TEM) or scanning electron microscopy (SEM). In this manner, the dimensions of the sample periodic structure can be estimated as similar to the reference periodic structure that has the expected damping rate closest to the acquired damping rate.

The system 100 can further include a processor 140 to process the data acquired by the detection system 130 and to perform the quality control described herein. In one example, the processor 140 can be integrated into the detection system 130 as shown in FIG. 1A. In another example, the processor 140 can be a separate processor in a computer, in which case the acquired data is transmitted to the computer for further processing.

Figure 2:
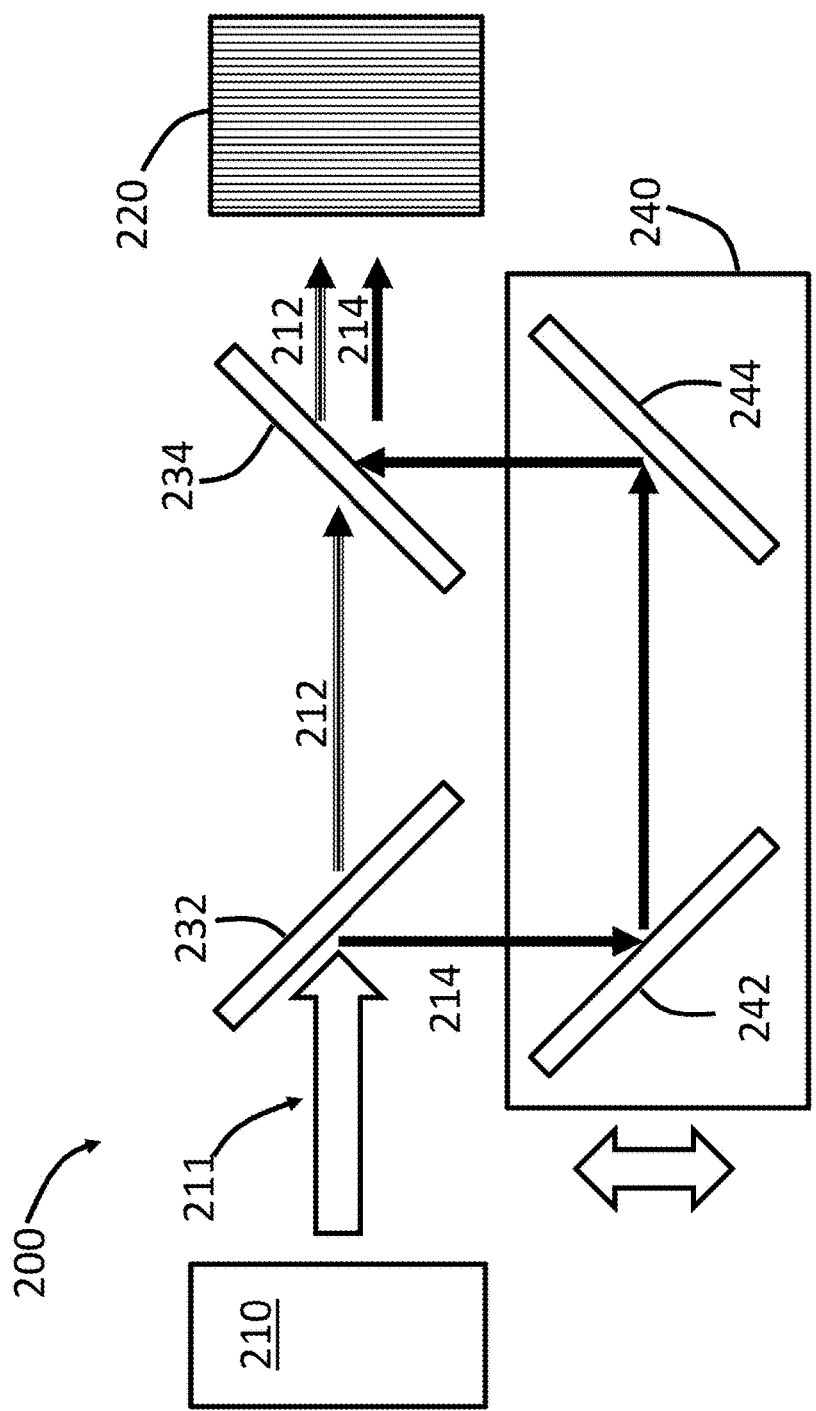
FIG. 2 shows a schematic of a light source to deliver excitation light pulses and probe light pulses for quality control of a periodic structure.

FIG. 2 shows a schematic of a system 200 including a laser 210 to provide both excitation light beams 212 and probe light beams 214 for quality control of a periodic structure 220. The laser 210 can include, for example, a Ti: Sapphire laser, an Nd: YAG laser, a fiber laser, or any other appropriate laser. A beam splitter 232 is used in the system to split the laser output 211 into the excitation light beams 212 and the probe light beams 214. The percentage of beam energy directed to the excitation light beams 212 can be about 80% to about 99% (e.g., about 80%, about 85%, about 90%, about 95%, about 97%, or about 99%, including any values and sub ranges in between). The original laser output 211 can include a train of laser pulses. The repetition rate of the laser output 211 can be substantially equal to or greater than 1 kHz (e.g., about 1 kHz, about 2 kHz, about 5 kHz, about 10 kHz, about 20 kHz, about 50 kHz, about 100 kHz, about 200 kHz, about 500 kHz, or greater, including any values and sub ranges in between).

The excitation light beams 212 are transmitted to the periodic structure 220 via an optional beam splitter 234. The probe light beams 214 are transmitted to a delay stage 240 to adjust the delay of the probe light beams 214. For example, the delay stage 240 can include two reflectors 242 and 244 that can be moved along (or opposite) the incident direction of the probe light beams 214 so as to change the time delay of the probe light beams 214. Alternatively or additionally, the time delay of the probe light beams 214 can be controlled via an electro-optic crystal (not shown) to change the optical path length of the probe light beams 214.

In one example, the excitation light beams 212 and the probe light beams 214 are combined via the beam splitter 234 before being delivered to the periodic structure. In another example, the system 200 can work without the beam splitter 234. In this case, probe light beams 214 can be directed to the periodic structure by, for example, tilting the reflector 244.

Methods for Quality Control of Periodic Structures

Figure 3:
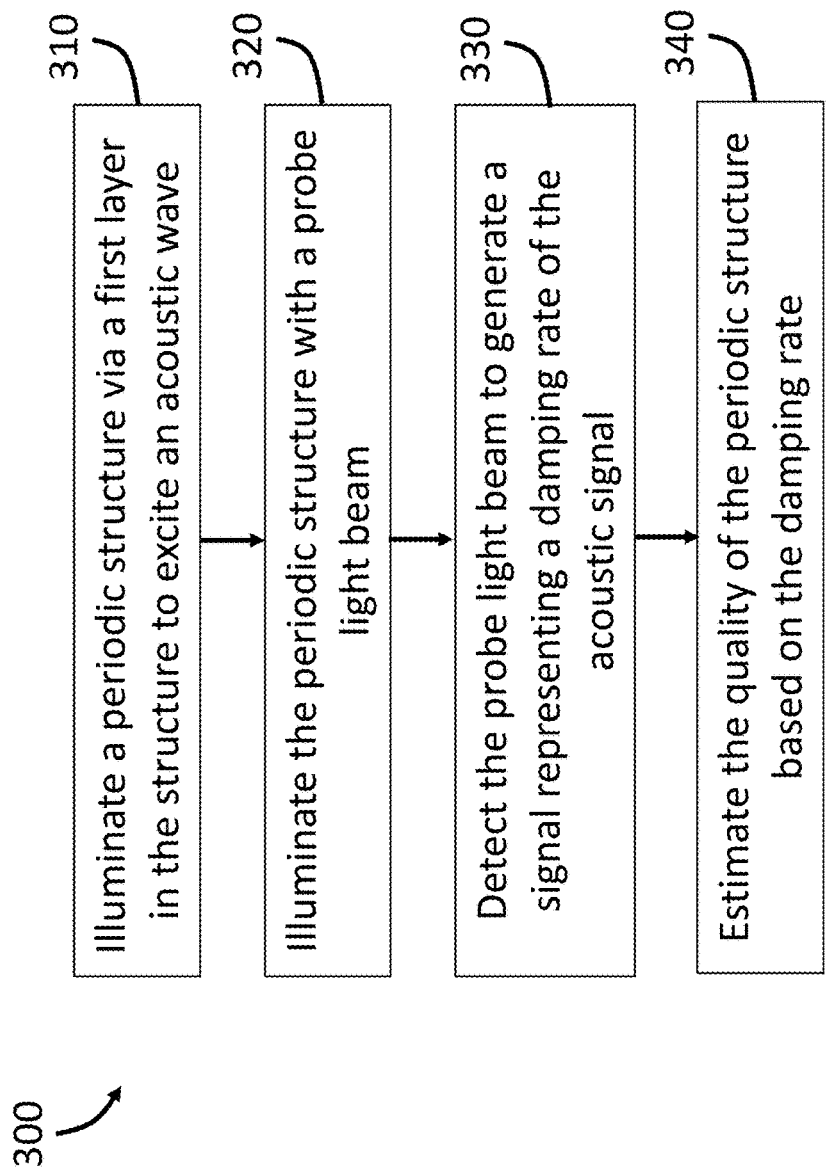
FIG. 3 illustrates a method for quality control of a periodic structure based on the damping rate of acoustic waves excited in the periodic structure.

FIG. 3 illustrates a method 300 of quality control of a periodic structure including a stack of layers. The method 300 includes illuminating the periodic structure through a first layer in the stack of layers with an excitation light beam so as to excite an acoustic wave in the periodic structure, at 310. At 320, a probe light beam is delivered to the periodic structure to measure the acoustic wave generated at 310. The method 300 also includes detecting the probe light beam, using a photodetector, after interaction with the periodic structure, to generate a signal representing the damping rate of the acoustic wave, at 330. The acquired damping rate is then employed to estimate the quality of the periodic structure, at 340.

The excitation light beam used in the method 300 can have a pulse duration substantially equal to or less than 1 ns (e.g., about 1 ns, about 500 ps, about 200 ps, about 100 ps, about 50 ps, about 20 ps, about 10 ps, about 5 ps, about 1 ps, about 500 fs, about 300 fs, about 200 fs, about 100 fs, or less, including any values and sub ranges in between). The method 300 can further include generating the excitation light beam using a laser, such as a Ti: Sapphire laser, an Nd: YAG laser, a fiber laser, or any other appropriate laser.

In some examples, the probe light beam can include a sequence of probe light pulses, each of which has a distinct time delay with respect to the excitation light beam. Each probe light pulse, after interaction with the periodic structure, is detected to compile a temporal signal illustrating the temporal evolution of the acoustic wave. In other words, each probe light pulse is employed to take a snap shot of the acoustic wave at a distinct timing point.

The excitation light beam can also include a sequence of excitation light pulses, each of which corresponds to a respective probe light pulse to form an excitation/probe pair. Each excitation/probe pair has a distinct time delay between the excitation light pulse and the probe light pulse in that pair. In other words, each time a measurement is performed with a probe light pulse, the acoustic wave is generated by the corresponding excitation light pulse. The acoustic waves generated by different excitation light pulses may differ, thereby creating fluctuations in the measured signal. To alleviate this issue, multiple measurements can be performed at each time delay with a group of excitation/probe pairs to generate an averaged signal. Different groups of excitation/probe pairs can have different time delays to capture the temporal profile of the acoustic signal.

In the method 300, the acoustic signal can be measured by detecting the probe light beam after transmission through the periodic structure. Alternatively, the probe light beam reflected from the periodic structure can also be detected to measure the acoustic signal.

The quality of the periodic structure can be manifested by several parameters. In one example, the method 300 includes estimating a period variation of the periodic structure. The period variation can refer to the deviation of the thickness of one or more layers from an expected thickness. The resolution of the estimation can be substantially equal to or less than 5 nm (e.g., about 5 nm, about 4 nm, about 3 nm, about 2 nm, about 1 nm, about 0.5 nm, or less, including any values and sub ranges in between). In other words, any deviation on the order of the resolution can be detected by the method 300.

In another example, the method 300 includes estimating the flatness of interfaces between adjacent layers in the periodic structure. The detectable deviation from an expected flatness can be on the nanoscale or sub-nanoscale (e.g., about 5 nm, about 4 nm, about 3 nm, about 2 nm, about 1 nm, about 0.5 nm, or less, including any values and sub ranges in between).

The quality estimation of the periodic structure can be performed in several ways. In one example, the acquired damping rate is compared with a reference damping rate of a reference acoustic signal in a reference periodic structure. The dimension of the reference periodic structure is also measured via, for example, an electron microscope (e.g., a TEM or an SEM). The reference periodic structure having the reference damping rate closest to the acquired damping rate can be regarded as having a similar dimension to the periodic structure under quality control.

In another example, a fast quality control procedure can be performed by comparing the acquired damping rate with a threshold damping rate. If the acquired damping rate is greater than the threshold damping rate, the corresponding periodic structure (or any device including the periodic structure) is designated as defective and a message indicating so can be generated.

Characterizations of Quality Control of Periodic Structures

Figures 4A, 4B:
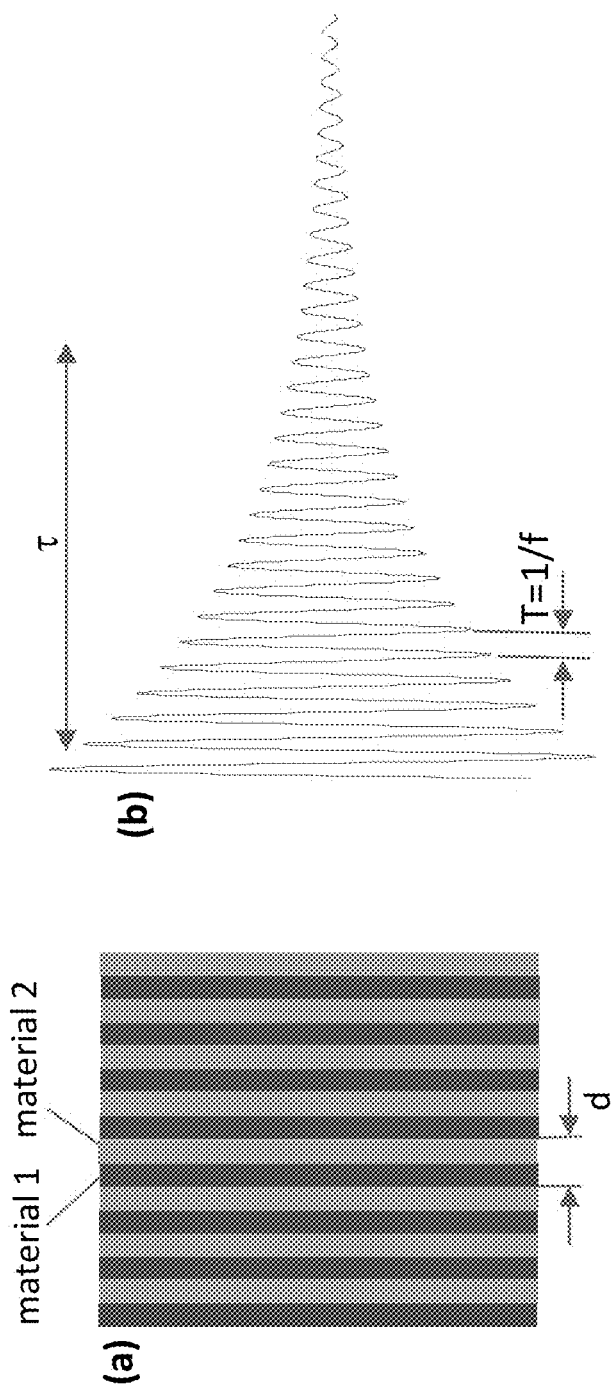
FIG. 4A shows a schematic of the superlattice structure used for characterizing the quality control method and system based on the damping rate of acoustic signals.
FIG. 4B shows a typical acoustic signal excited in the superlattice structure shown in FIG. 4A.

The quality control system and method described above was characterized using a superlattice structure. FIG. 4A shows a schematic of the suplerlattice structure including alternating layers made of material 1 (e.g., InGaN) and material 2 (e.g., GaN). FIG. 4B shows a typical acoustic signal excited in the superlattice structure by an excitation light beam and measured using a probe light beam as described above. Femtosecond laser pulses can be used to generate acoustic waves in the superlattice structure. The period of acoustic oscillations T is determined by the average period d of the superlattice structure. The decay time of acoustic oscillations τ depends on the statistical non-uniformity of the layer thickness. In general, a shorter decay time τ indicates a larger non-uniformity of the layer thickness and, consequently, poor quality of the structure. In contrast, a longer decay time τ usually indicates less non-uniformity and a higher structure quality. A quantitative relationship between the acoustic decay time τ and statistical characteristics, such as root mean square (RMS) variation of the layer thickness, can be established experimentally by correlating laser acoustic measurements with transmission electron microscopy (TEM) images or theoretically by modeling acoustic wave propagation in a structure with a statistical variation in the layer thickness.

Figures 5A, 5B:
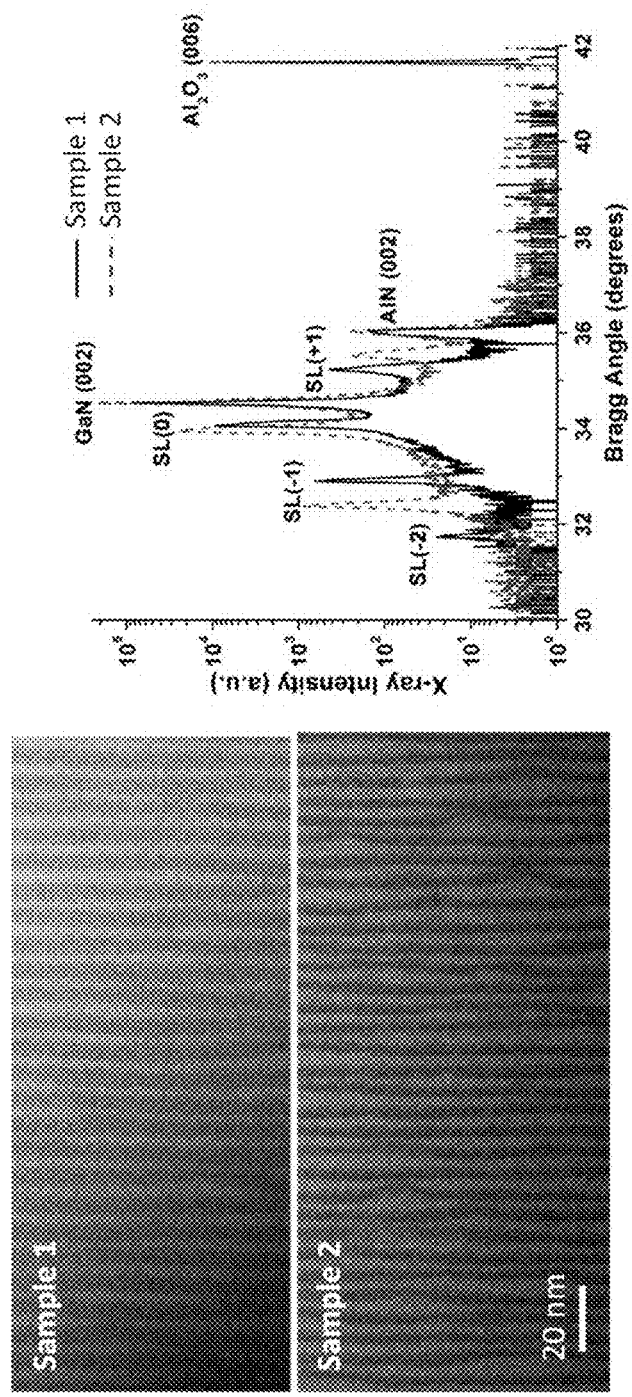
FIG. 5A are transmission electron microscopy (TEM) images of two InGaN/GaN superlattice structures having different degrees of small-scale non-uniformity.
FIG. 5B shows x-ray diffraction (XRD) spectra of the two superlattice structures shown in FIG. 5A.

As described above, thin layers used in the fabrication of semiconductor devices tend to have thickness variations on the scale of tens of nanometers or less, which is usually much smaller than a typical laser spot size. FIG. 5A shows TEM images of two InGaN/GaN superlattice structures having different degree of small-scale thickness non-uniformity. Both superlattice structures include 100 periods (i.e., 200 alternating layers of InGaN and GaN), each of which was grown via molecular beam epitaxy. The samples were expected to have a period thickness of about 8 nm. It can be observed from the TEM images that sample 2 is characterized by a much greater degree of non-uniformity, with some layers being discontinuous.

FIG. 5B shows x-ray diffraction (XRD) spectra of the two samples shown in FIG. 5A. The two spectra from the two samples are very similar, thereby obscuring the different levels of non-uniformity between them. The only feature of the XRD spectrum of sample 2 indicating its poorer uniformity is the absence of the weak SL(−2) peak.

To generate and detect acoustic waves, a femtosecond pump-probe configuration was constructed using an amplified Ti: Sapphire laser system. The laser output had a pulse duration of about 200 fs and a repetition rate at about 250 kHz. The laser output was frequency-doubled to 390 nm and then split into the excitation beam and the variably delayed probe pulses. The excitation beam was modulated by an acousto-optic modulator at 93 kHz frequency to facilitate lock-in detection and focused to a spot of about 50 μm in diameter at the sample. The probe beam was focused to an about a spot of about 25 μm in diameter at the center of the excitation spot. After passing through the sample, the probe beam was directed to a photodiode, which detected the probe beam and transmitted the detected signal into a lock-in amplifier. The photodiode signal plotted as a function of the delay time contained a large slow component due to the electronic response and the fast oscillating component due to acoustic waves. The acoustic component of the signal was isolated by subtracting the slow background.

FIG. 6A and 6C show the acoustic component of the signal from samples 1 and 2, respectively. FIGS. 6B and 6D show the spectral signals acquired by Fourier transform of the signal shown in FIG. 6A and 6C, respectively. It can be observed that the decay time of the acoustic oscillations measured at 1/e level is about 50 ps in sample 1 and about 6 ps in sample 2. The difference of decay times in these two samples is almost an order of magnitude. This shows that the decay time can be a sensitive indicator of sample irregularity.

The damping rates of the acoustic signals shown in FIGS. 6A and 6C can be calculated by taking the Fourier transform of the acoustic signals. The linewidths of the spectral peaks in the spectral signals (shown in FIGS. 6B and 6D) indicates the damping rates. A wider spectral peak indicates a shorter delay time and accordingly a poorer quality of the corresponding superlattice structure.

As demonstrated by FIGS. 4A-6D, the non-uniformity of the layer thickness of a periodic structure can be characterized by TEM or XRD. However, TEM is a time-consuming and destructive method. XRD is a non-contact technique.

Comparing FIG. 5B with FIGS. 6A-6D reveals that the laser acoustic measurements have a much higher sensitivity to irregularities in the layer thickness. The XRD spectra from samples 1 and 2 look very similar, with the only noticeable difference being the absence of the weak second-order SL peak in the sample 2 spectrum. Laser acoustic measurements, in contrast, yield a drastic difference between samples 1 and 2.

The systems and methods described herein can be used to monitor the performance of manufacturing equipment that is used to fabricate multilayer semiconductor structures. These semiconductor structures can include, for example, GaN-based structures for blue LEDs and blue laser diodes as well as GaAs- and InP-based structures for quantum cascade lasers. The described approach can also be implemented, for example, using the commercially available picosecond acoustic thin film metrology system Metapulse produced by Rudolph Technologies.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of"0 and "consisting essentially of" shall be closed or semi-closed transitional phrases, respectively, as set forth in the United States Patent Office Manual of Patent Examining Procedures, Section 2111.03.

The invention claimed is:

1. A method of quality control of a periodic structure comprising a stack of layers, the method comprising:
    illuminating the periodic structure through a first layer in the stack of layers with at least one excitation light beam, the at least one excitation light beam exciting an acoustic wave in the periodic structure;
    illuminating the periodic structure with at least one probe light beam;
    detecting the at least one probe light beam, using a photodetector, after interaction with the periodic structure, the photodetector being configured to generate a signal representing a damping rate of the acoustic wave; and
    estimating, with a processor, non-uniformity of the periodic structure based at least in part on the damping rate of the acoustic wave in the periodic structure,
    wherein estimating the non-uniformity of the periodic structure comprises estimating a period variation of the periodic structure, and
    wherein estimating the period variation of the periodic structure comprises detecting a deviation in a period of the periodic structure substantially equal to or less than 5 nm from an expected period of the periodic structure.

2. The method of claim 1, further comprising:
    generating the excitation light beam with a pulse duration substantially equal to or less than 1 ns.

3. The method of claim 1, wherein the at least one probe light beam comprises a sequence of probe light pulses, each probe light pulse in the sequence of probe light pulses having a distinct time delay with respect to the at least one excitation light beam, and wherein detecting the at least one probe light beam comprises detecting each probe light pulse as a function of the distinct time delay.

4. The method of claim 1, wherein the at least one excitation light beam comprises a sequence of excitation light pulses and the at least one probe light beam comprises a sequence of probe light pulses, each probe light pulse in the sequence of probe light pulses having a distinct time delay with respect to a corresponding excitation light pulse in the sequence of excitation light pulses.

5. The method of claim 1, wherein detecting the probe light beam comprises detecting the probe light beam transmitted through the periodic structure.

6. The method of claim 1, wherein detecting the probe light beam comprises detecting the probe light beam reflected from the periodic structure.

7. The method of claim 1, wherein the periodic structure comprises a semiconductor superlattice.

8. A method of quality control of a periodic structure comprising a stack of layers, the method comprising:
    illuminating the periodic structure through a first layer in the stack of layers with at least one excitation light beam, the at least one excitation light beam exciting an acoustic wave in the periodic structure;
    illuminating the periodic structure with at least one probe light beam;
    detecting the at least one probe light beam, using a photodetector, after interaction with the periodic structure, the photodetector being configured to generate a signal representing a damping rate of the acoustic wave;
    estimating, with a processor, non-uniformity of the periodic structure based at least in part on the damping rate of the acoustic wave in the periodic structure,
    wherein estimating the non-uniformity of the periodic structure comprises estimating a flatness of interfaces between adjacent layers in the stack of layers, and
    wherein estimating the flatness of the interfaces comprises detecting a deviation from an expected flatness substantially equal to or less than 5 nm.

9. A method of quality control of a periodic structure comprising a stack of layers, the method comprising:
    illuminating the periodic structure through a first layer in the stack of layers with at least one excitation light beam, the at least one excitation light beam exciting an acoustic wave in the periodic structure;
    illuminating the periodic structure with at least one probe light beam;
    detecting the at least one probe light beam, using a photodetector, after interaction with the periodic structure, the photodetector being configured to generate a signal representing a damping rate of the acoustic wave;
    estimating, with a processor, non-uniformity of the periodic structure based at least in part on the damping rate of the acoustic wave in the periodic structure, wherein estimating the non-uniformity of the periodic structure comprises comparing the damping rate of the acoustic signal with a reference damping rate of a reference acoustic signal in a reference periodic structure;
    measuring a dimension of the reference periodic structure; and
    measuring the reference damping rate of the reference acoustic signal in the reference periodic structure.

10. The method of claim 9, wherein measuring the dimension of the reference periodic structure comprises measuring the dimension using an electron microscope.

11. A method of quality control of a periodic structure comprising a stack of layers, the method comprising:
    illuminating the periodic structure through a first layer in the stack of layers with at least one excitation light beam, the at least one excitation light beam exciting an acoustic wave in the periodic structure;
    illuminating the periodic structure with at least one probe light beam;
    detecting the at least one probe light beam, using a photodetector, after interaction with the periodic structure, the photodetector being configured to generate a signal representing a damping rate of the acoustic wave; and
    estimating, with a processor, non-uniformity of the periodic structure based at least in part on the damping rate of the acoustic wave in the periodic structure,
    wherein estimating the non-uniformity of the periodic structure comprises comparing the damping rate with a threshold damping rate, and the method further comprises:
    in response to determining that the damping rate is greater than the threshold damping rate, generating a message indicating that the periodic structure is defective.

12. An apparatus for evaluating non-uniformity of a periodic structure comprising a stack of layers, the apparatus comprising:
    at least one light source configured to illuminate the periodic structure through a first layer in the stack of layers with an excitation light beam, the excitation light beam exciting an acoustic wave in the periodic structure, the at least one light source further configured to illuminate the periodic structure with a probe light beam;
    a detection system, in optical communication with the periodic structure, configured to detect the probe light beam after interaction with the periodic structure, the detection system further configured to generate a signal representing a damping rate of the acoustic wave in the periodic structure, the damping rate of the acoustic wave representing the non-uniformity of the periodic structure; and
    a processor, operably coupled to the detection system, to estimate the non-uniformity of the periodic structure based on the damping rate of the acoustic wave, wherein the processor is configured to estimate the non-uniformity of the periodic structure by estimating a period variation of the periodic structure and configured to estimate the period variation of the periodic structure by detecting a deviation in a period of the periodic structure substantially equal to or less than 5 nm from an expected period of the periodic structure.

13. The apparatus of claim 12, wherein the at least one light source is configured to emit the excitation light beam with a pulse duration substantially equal to or less than 1 ns.

14. The apparatus of claim 12, wherein the at least one light source is configured to emit the probe light beam with a pulse duration substantially equal to or less than 1 ns and the probe light beam is variably delayed with respect to the excitation light beam.

15. The apparatus of claim 12, wherein the detection system is configured to measure the probe light beam transmitted through the periodic structure.

16. The apparatus of claim 12, wherein the detection system is configured to measure the probe light beam reflected from the periodic structure.

* * * * *